(12) United States Patent
Kettner et al.

(10) Patent No.: US 10,420,692 B2
(45) Date of Patent: Sep. 24, 2019

(54) RADIOLUCENT SURGICAL POSITIONING SYSTEM

(71) Applicant: MATCH GRADE MEDICAL LLC, Neenah, WI (US)

(72) Inventors: David M. Kettner, Greenville, WI (US); Robert P. Limoni, Green Bay, WI (US)

(73) Assignee: Match Grade Medical LLC, Neenah, WI (US)

( * ) Notice: Subject to any disclaimer, the term of this patent is extended or adjusted under 35 U.S.C. 154(b) by 246 days.

(21) Appl. No.: 15/354,238

(22) Filed: Nov. 17, 2016

(65) Prior Publication Data

US 2017/0135891 A1    May 18, 2017

Related U.S. Application Data

(60) Provisional application No. 62/256,351, filed on Nov. 17, 2015.

(51) Int. Cl.
| | |
|---|---|
| *A61G 13/12* | (2006.01) |
| *A61G 13/00* | (2006.01) |
| *A61B 6/04* | (2006.01) |

(52) U.S. Cl.
CPC ........ *A61G 13/1295* (2013.01); *A61B 6/0421* (2013.01); *A61G 13/0081* (2016.11); *A61G 13/12* (2013.01); *A61G 13/123* (2013.01); *A61G 2210/50* (2013.01)

(58) Field of Classification Search
CPC ........................................................ A61G 13/12
USPC ............................................. 5/601, 621–624
See application file for complete search history.

(56) References Cited

U.S. PATENT DOCUMENTS

| | | | | |
|---|---|---|---|---|
| 3,873,081 A * | 3/1975 | Smith | .................... | A61G 13/12 5/621 |
| 5,289,603 A * | 3/1994 | Kumagai | ............... | A61G 7/065 128/869 |
| 6,026,812 A * | 2/2000 | Lipson | .................. | A61F 5/0585 128/882 |
| 9,254,179 B2 | 2/2016 | Limoni et al. | | |
| 2003/0167569 A1* | 9/2003 | Newkirk | ................ | A61G 13/12 5/613 |

* cited by examiner

*Primary Examiner* — Fredrick C Conley
(74) *Attorney, Agent, or Firm* — Boyle Fredrickson S.C.

(57) ABSTRACT

A surgical support system provides a set of paddles receivable by a pegboard to provide larger area skin-supporting surfaces as stabilized by a pair of pegs received in the pegboard. The paddles may be primarily constructed of an autoclavable radiolucent polymer with short aluminum pegs in their lower ends for being received in the pegboard.

14 Claims, 4 Drawing Sheets

RADIOLUCENT SURGICAL POSITIONING SYSTEM

STATEMENT REGARDING FEDERALLY SPONSORED RESEARCH OR DEVELOPMENT

—

CROSS REFERENCE TO RELATED APPLICATION

This application claims the benefit of U.S. provisional 62/256,351 filed Nov. 17, 2015, and hereby incorporated by reference.

BACKGROUND OF THE INVENTION

The present invention relates to a patient positioning apparatus and in particular to a set of improved paddles for use with a surgical, pegboard positioner. For many medical procedures, for example, an orthopedic procedure such as hip arthroplasty, it is important to stabilize the patient against on the table against movement resulting from forces applied to the patient during the procedure.

One versatile stabilizing approach places a pegboard on the surgical table, held to the table, for example, by rail clamps. U.S. Pat. No. 9,254,179, naming the present inventors and hereby incorporated by reference, describes a pegboard of this type such as is also available through a number of commercial suppliers including, for example, the David Scott company of Framingham, Mass., USA.

The pegboard provides a polymer plate having regularly spaced holes bored vertically in its surface to receive corresponding pegs that may extend upward from the holes adjacent to the patient where support is required. These pegs include aluminum shafts sized to, be received with sliding fit in the regularly spaced holes of the pegboard. The shaft may be covered with a coating of rubber having a generally circular horizontal cross-section.

SUMMARY OF THE INVENTION

The present invention provides an improved peg (paddle) that provides a broader surface supported by two pegs received in the pegboard greatly reducing concentrated pressure on the patient such as can produce a pressure ulcer. The wider paddles permit the aluminum pegs to be truncated in height providing improved transparency to x-rays that may be required during certain orthopedic procedures. The wider paddles also eliminate the need for the cushioning provided by rubber such as can prevent the paddles from being readily sterilized in an autoclave.

Specifically, the invention in one embodiment provides a surgical positioning system for use with the pegboard of a type having an upper surface for support of a patient and including regularly spaced vertical bore holes. This positioning system provides a set, of paddle elements attachable to the pegboard to extend upward therefrom, a lower end of each paddle element including at least two pegs slidably receivable within corresponding vertical bore holes of the pegboard and an upper end of each paddle element being constructed of a radiolucent polymer. Each paddle element provides a noncircular horizontal cross-section as attached to the pegboard presenting a broad lateral surface for contact with the skin of the patient.

It is thus a feature of at least one embodiment of the invention to provide an improved patient support paddle providing reduced contact pressure with the patient and radiolucency using multi-peg support.

The pegs are aluminum cylinders.

It is thus a feature of at least one embodiment of the invention to provide a radiolucent paddle that nevertheless provides for the robust attachment provided by an aluminum polymer pegboard sliding fit.

The pegs may extend into the radiolucent polymer by less than 2.5 inches from an upper surface of the pegboard when the paddle is installed in the pegboard.

It is thus a feature of at least one embodiment of the invention to make use of the stronger upper paddle providing low-pressure patient contact to reduce the peg length improving radiolucency of the critical upper portions of the paddle.

The radiolucent polymer maybe autoclavable at 273 degrees Fahrenheit without damage.

It is thus a feature of at least one embodiment of the invention to provide a peg system that can be sterilized.

An upper end of at least one paddle may include at least two upwardly extending bore holes for receiving pegs of a second paddle to attach the second paddle to the at least one paddle.

It is thus a feature of at least one embodiment of the invention to permit a stacking of paddles to provide greater versatility in supporting the patient and greater contact area with the patient's skin.

The sidewalls of the paddle installed in the pegboard may include concave opposed cutouts for fitting in between legs of a patient.

It is thus a feature of at least one embodiment of the invention to provide a paddle that may fit between the patient's legs while maximizing support area.

These particular objects and advantages may apply to only some embodiments falling within the claims and thus do not define the scope of the invention.

DETAILED DESCRIPTION OF THE PREFERRED EMBODIMENT

Figure 1A:
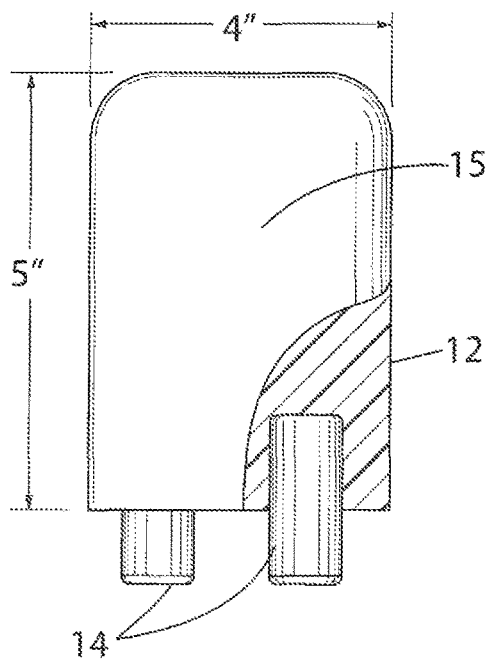
FIGS. 1a-1e are a front elevational view in partial cross-section, a side elevational view, a bottom plan view, a top plan view and a perspective view of a first paddle design intended for general use according to the present invention.
Figure 1B:
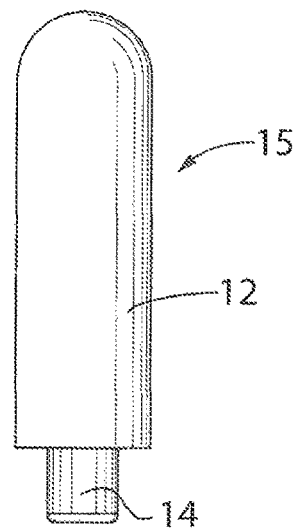
Figure 1C:
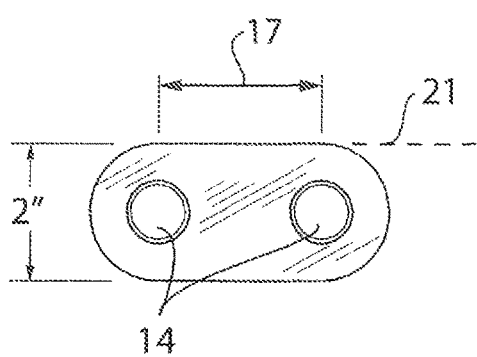
Figure 1D:
Figure 1E:
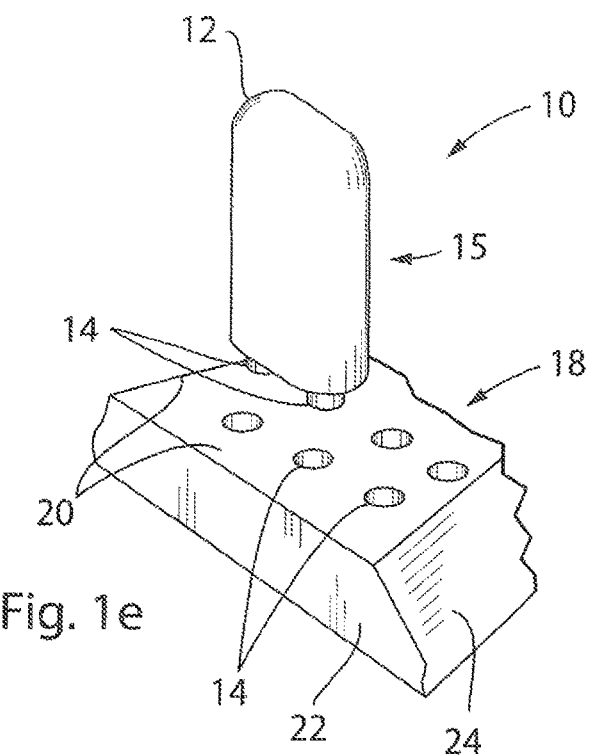

Referring now to FIGS. 1a-1e, a surgical positioning pegboard system 10 is designed to eliminate pressure points and offer radiolucency by providing a noncircular cross-section paddle 12. The pegboard system 10 provides one or more paddles 12 having downwardly extending cylindrical pegs 14 that may be received within corresponding holes 16 in a pegboard 18. The holes 16 may have one-inch diameters and may be arranged generally in rectilinear rows and columns separated by two inches on center. As so arranged, the holes 16 may accept in sliding fit two or more downwardly extending cylindrical pegs 14 of a given paddle 12 with the two or more mounting pegs 14 aligned parallel or perpendicular to the longitudinal edge 22 of the pegboard 18 extending generally along the longest dimension of the pegboard 18.

The holes 16 extend along axes that are generally perpendicular to a generally planar top face 20 of the pegboard 18, the latter of which may be constructed of a polymer material such as extruded polyethylene. The pegboard 18 may be attached to the upper surface of a surgical table or the like through clamps to present a generally horizontal upper surface. The ends 24 of the pegboard 18 are tapered to, reduce pressure points on the patient that may extend off the end of the board.

An upper body 15 of each paddle 12 may be constructed from, a solid, homogenous, acetal copolymer (Polyoxymethylene) to provide a generally radiolucent structure. Acetal gives a smooth, low friction surface and rigid support. It can be sterilized at 273 degrees Fahrenheit using a standard medical autoclave. The cylindrical pegs 14 extending from the lower end of the body 15 may be press fit cylindrical aluminum mounting pegs 14 for strength and ease of insertion.

In one embodiment, the paddle 12 may have a width of four inches, a height of at least live inches and desirably being provided in regular sizes of six, nine, and 12 inches and a thickness of two inches. The body of the paddle 12 has a noncircular cross-section for most of its height, as visible from the bottom view of FIG. 1c providing a substantially flat face 17 extending horizontally along an axis 21 and vertically from the pegboard 18 when the paddle 12 is installed in the pegboard 18. Generally, this flat face 17 continues by at least two inches in width horizontally along axis 21 without deviation perpendicular to axis 21 by more than a quarter inch and preferably without deviation by more than ⅛ inch along its horizontal extent. Deviation from absolute flatness recognizes some compliance in the skin and tissue of the patient yet still provides a greatly reduced pressure such as could create pressure ulcers.

The width of the paddle 12 is sufficient along axis 21 to support two cylindrical pegs 14 each having a one-inch diameter separated on center by two inches, a center point between the two cylindrical pegs 14 centered in the cross-section. In this regard, the body of the paddle 12 conforms generally to a rectangular parallelepiped rounded on its left and right edges and, top surface with a one-inch diameter radius having four vertical sidewalls when the paddle 12 is installed in the pegboard 18 oriented as described above.

Two aluminum pegs 14 protruding from the bottom of the paddle 12 give a high-strength mounting system that is easy to assemble. The aluminum pegs 14 extend approximately 2.5 inches into the bottom of the paddle 12 (and thus 2.5 inches above the surface of the pegboard 18 when the paddle 12 is installed on the pegboard 18) giving the paddle 12 sufficient mechanical support without interfering with typical x-ray requirements for total hip arthroplasty in the upper body 15. Specifically, the entirety of the paddle 12 above 2.5 inches over the surface of the pegboard 18 may be substantially transparent to x-rays. The use of multiple mounting pegs 14 eliminates rotation of the paddle 12 resulting in more controlled support of the patient.

Figure 2:
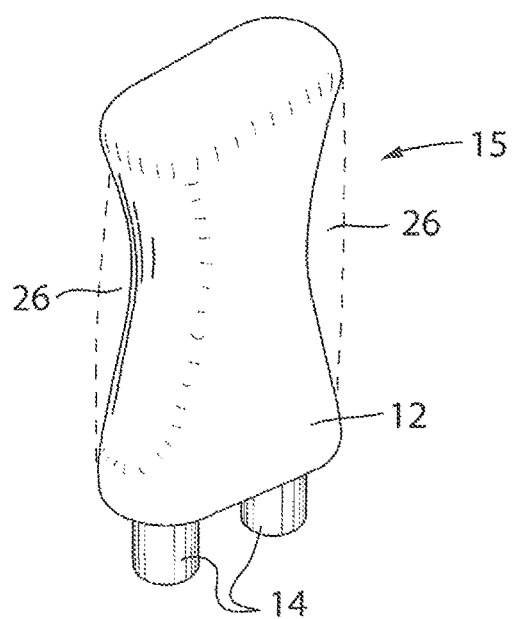
FIG. 2 is a perspective view of a second paddle design having substantially identical top and bottom plan views as the paddle design of FIG. 1, the second paddle design intended for use between a patient's legs and having leg receiving cutouts.
Figure 3A:
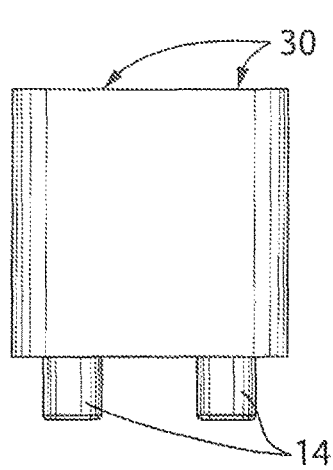
FIGS. 3a-3d are a front elevational view, a side elevational view, a top view and a perspective view of a third paddle design having a substantially identical bottom plan view as the paddle design of FIG. 1 providing an extender for use with another paddle to increase its length.
Figure 3B:
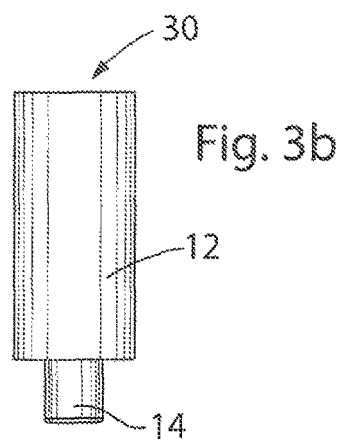
Figure 3C:
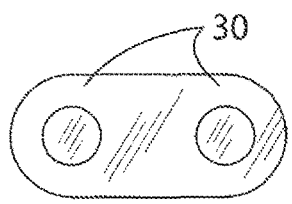
Figure 3D:
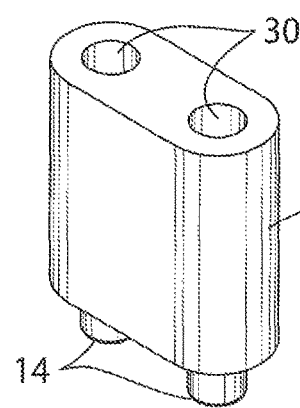

Paddles 12 are designed in several configurations (angled, tapered, curves and projections, straight, extensions, differing, heights) as shown for specific uses and correct anatomical interface with the patient. For example, as shown in FIG. 2, the left and right sides of the paddle 12 may include concave cutouts 26, for example, so that the paddle 12 may fit between the patient's legs with the legs lying within the approximately equal diameter cutouts 26. The cutouts are in the narrow vertical walls of the paddle 12 preserving a broader face for high-pressure contact with the patient.

Figure 4A:
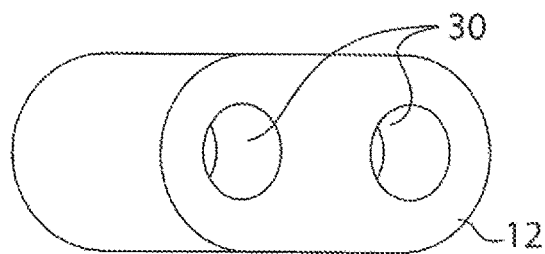
FIGS. 4a-4c are a top plan, a side elevational view in partial cross-section and a perspective view of a fourth paddle design having a bottom plan view substantially identical to that of the paddle of FIG. 1.
Figure 4B:
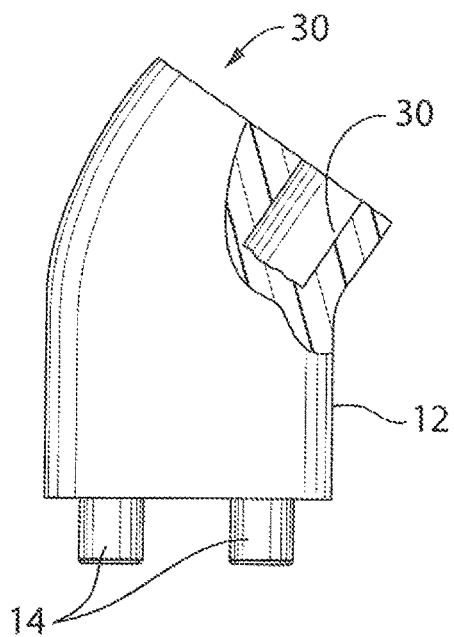
Figure 4C:
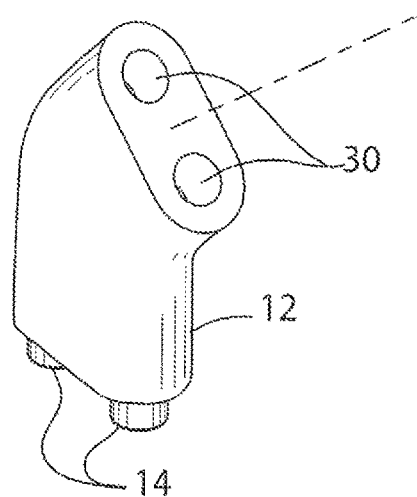

Referring to FIGS. 3 and 4, the invention also can provide extender paddles 12 having upwardly open secondary holes 30 (flat bottomed blind bores) that may receive the pegs 14 of another paddle 12 to extend the other paddle 12 upward in height either in a straight line or at an angle. So for example, the holes 30 of the extender of FIG. 3 are axially aligned with the pegs 14 while the holes 30 of the extender of FIG. 4 are canted at approximately 45 degrees with respect to axes of the pegs 14 within a plane of separation of the pegs 14. Although the look of the upper portion of the paddles 12 will have angles and edges suited to a specific application, the wide flat surface on the face of the paddle 12 and the unique shape of the base of the paddle 12 preserve the benefits described above.

Figure 5:
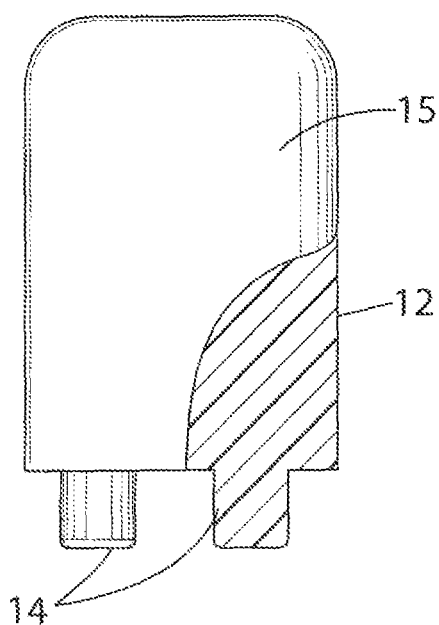
FIG. 5 is a figure similar to that of FIG. 1a showing a single piece paddle providing improved, radiolucency and sterilizing.

Referring now to FIG. 5, in one embodiment, the paddles 12 may have downwardly extending cylindrical pegs 14 that are formed integrally with the upper body 15 of the paddle 12, for example, as machined out of a single block of polymer material. In all other respects the dimensions of the paddle 12 may be the same as that described above with respect to FIG. 1. Although not shown, certain paddles 12, particularly those which will not have substantial torques about a vertical axis, may have a single downwardly extending cylindrical pegs 14 centered on a central axis of the upper body 14

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified, forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A surgical positioning system for use with a pegboard providing an upper surface for support of a patient, the upper surface including regularly spaced vertical bore holes, the surgical positioning system comprising:
    at least one paddle element attachable to the pegboard to extend upward therefrom, the at least one paddle element having:
        a lower end of the at least one paddle element including at least one peg slidably receivable within a corresponding vertical bore hole of the pegboard and
        an upper end of each paddle element including a body having at least two substantially flat faces extending along first and second parallel planes flanking the at least one peg, the flat faces joined by curved convex ends, and
        wherein the upper and lower ends of the paddle element are constructed of a unitary, integrally formed radiolucent polymer;
        wherein the paddle elements provide a noncircular horizontal cross-section as attached to the pegboard presenting a broad lateral surface for contact with skin of the patient.

2. The surgical positioning system of claim 1 providing at least two downwardly extending pegs spaced to be received within corresponding adjacent vertical bore holes of the pegboard.

3. The surgical positioning system of claim 2 wherein the pegs extend into the radiolucent polymer by less than 2.5 inches from an upper surface of the pegboard when the paddle is installed in the pegboard.

4. The surgical positioning system of claim 1 wherein the radiolucent polymer is autoclavable at 273 degrees Fahrenheit without damage.

5. The surgical positioning system of claim 4 wherein the polymer is acetal copolymer (Polyoxymethylene).

6. The surgical positioning system of claim 1 wherein the broad lateral surface extends laterally for a distance of at least two inches.

7. The surgical positioning system of claim 1 wherein a side wall of the paddle installed in the pegboard includes a horizontally directed concave cutout for fitting against a leg of a patient.

8. The surgical positioning system of claim 1 further including the pegboard.

9. The surgical positioning system of claim 8 further including multiple paddle elements each having a height installed in the pegboard of at least five inches.

10. The surgical positioning system of claim 1 wherein the paddle has a height of at least five inches.

11. The surgical positioning system of claim 1 wherein sidewalls of the paddle as installed in the pegboard are vertical.

12. A surgical positioning system for use with a pegboard providing an upper surface for support of a patient, the upper surface including regularly spaced vertical bore holes, the surgical positioning system comprising:
    at least one paddle element attachable to the pegboard to extend upward therefrom, a lower end of the at least one paddle element including at least one peg slidably receivable within a corresponding vertical bore hole of the pegboard and an upper end of each paddle element being constructed of a radiolucent polymer;
    wherein the paddle elements provide a noncircular horizontal cross-section as attached to the pegboard presenting a broad lateral surface for contact with skin of the patient
    wherein an upper end of at least one paddle includes at least two upwardly extending bore holes for receiving pegs of a second paddle to attach the second paddle to the at least one paddle.

13. The surgical positioning system of claim 12 wherein the upwardly extending bore holes are substantially parallel to axes of the pegs of the paddle.

14. The surgical positioning system of claim 12 wherein the upwardly extending bore holes are angled with respect to axes of the pegs of the paddle.

* * * * *